United States Patent
Ouyang (12) 
(10) Patent No.: US 11,071,323 B2
(45) Date of Patent: Jul. 27, 2021

(54) BATTERY ASSEMBLY AND ELECTRONIC CIGARETTE HAVING SAME

(71) Applicant: SHENZHEN IVPS TECHNOLOGY CO., LTD., Shenzhen (CN)

(72) Inventor: Junwei Ouyang, Shenzhen (CN)

(73) Assignee: SHENZHEN IVPS TECHNOLOGY CO., LTD., Guangdong (CN)

( * ) Notice: Subject to any disclaimer, the term of this patent is extended or adjusted under 35 U.S.C. 154(b) by 278 days.

(21) Appl. No.: 16/378,337

(22) Filed: Apr. 8, 2019

(65) Prior Publication Data

US 2019/0239568 A1 Aug. 8, 2019

(30) Foreign Application Priority Data

Feb. 8, 2018 (CN) .......................... 201810133323.6

(51) Int. Cl.
| | |
|---|---|
| *F22B 1/28* | (2006.01) |
| *A24F 40/40* | (2020.01) |
| *H01M 50/579* | (2021.01) |
| *A24F 40/10* | (2020.01) |
| *A24F 40/60* | (2020.01) |
| *A24F 40/90* | (2020.01) |

(52) U.S. Cl.
CPC ........... *A24F 40/40* (2020.01); *H01M 50/579* (2021.01); *A24F 40/10* (2020.01); *A24F 40/60* (2020.01); *A24F 40/90* (2020.01)

(58) Field of Classification Search
CPC .............................. C23C 16/4481; F22B 1/282
USPC ........................................... 165/164; 392/450
See application file for complete search history.

(56) References Cited

U.S. PATENT DOCUMENTS

| | | | | |
|---|---|---|---|---|
| 3,782,456 | A | * | 1/1974 | Gusmer ................ F28D 7/0041 165/164 |
| 4,692,592 | A | * | 9/1987 | Kale ................... F28D 20/0039 392/450 |
| 10,004,271 | B2 | * | 6/2018 | Li .......................... A24F 47/008 |
| 2018/0013175 | A1 | | 1/2018 | Liu |
| 2018/0166238 | A1 | | 6/2018 | Chen |
| 2018/0199631 | A1 | * | 7/2018 | Chen ....................... A24F 40/50 |

FOREIGN PATENT DOCUMENTS

| | | |
|---|---|---|
| CN | 204861170 U | 12/2015 |
| CN | 206507317 U | 9/2017 |
| CN | 107411175 A | 12/2017 |

(Continued)

*Primary Examiner* — Phuong Chi Thi Nguyen
(74) *Attorney, Agent, or Firm* — IP-PAL Patent US; Klaus Michael Schmid (57) ABSTRACT

A battery assembly and an electronic cigarette using the battery assembly are provided. The battery assembly comprises a main body and a rear cover fixedly installed to the main body. One end of the main body is provided with a connecting portion fixedly electrically connected to an external load, and the other end thereof is provided with an inner cavity for accommodating an electronic component. The rear cover is fixedly installed to the main body and covers the inner cavity. One end of the main body far from the connecting portion is provided with an extension toward the rear cover, and the extension covers the end of the rear cover far from the connecting portion, effectively preventing the phenomenon that a housing far from the end of a suction port is damaged by impact when the electronic cigarette is dropped.

18 Claims, 10 Drawing Sheets

(56) References Cited

FOREIGN PATENT DOCUMENTS

| | | |
|---|---|---|
| GB | 2560090 A | 1/2018 |
| WO | 2015157901 A1 | 10/2015 |
| WO | 2016054580 A1 | 4/2016 |

\* cited by examiner

BATTERY ASSEMBLY AND ELECTRONIC CIGARETTE HAVING SAME

TECHNICAL FIELD

The present invention relates to a battery assembly and an electronic cigarette using the battery assembly.

BACKGROUND

Electronic cigarettes, also known as electronic cigarettes, are mainly used to quit smoking and replace conventional cigarettes. It has an appearance and taste similar to conventional cigarettes, and even has more tastes than conventional cigarettes. It can generate smoke, a taste and a feel like conventional cigarettes. Without tar, suspension particles and other harmful components in conventional cigarettes, electronic cigarettes have gradually replaced conventional cigarettes in the market.

Because it is easy to carry small electronic cigarettes, they are loved by consumers. Therefore, various types of small electronic cigarettes appear on the market. At the same time, the housing of the small electronic cigarettes is prepared using the In Molding Label process to achieve a beautiful appearance. However, during the user's use, it is easy for the small electronic cigarettes to be dropped, and a housing far from the end of a suction port is susceptible to damage from impact.

SUMMARY

The main object of the present invention is to provide a battery assembly that is designed to prevent the phenomenon that a housing far from the end of a suction port is damaged by impact when the electronic cigarette is dropped.

In order to achieve the above object, a battery assembly according to the present invention comprises a main body and a rear cover fixedly installed to the main body, wherein one end of the main body is provided with a connecting portion fixedly electrically connected to an external load, and the other end thereof is provided with an inner cavity for accommodating an electronic component, the rear cover is fixedly installed to the main body and covers the inner cavity, one end of the main body far from the connecting portion is provided with an extension toward the rear cover, and the extension covers the end of the rear cover far from the connecting portion.

Preferably, the rear cover and the extension far from one end of the connecting portion are integrally connected in a curved smooth transition manner.

Preferably, at least one connecting buckle and at least one connecting female buckle are provided at both ends of one of the main body and the rear cover, respectively, at least one connecting neck and at least one connecting sub-buckle are correspondingly provided at both ends of the other of the main body and the rear cover, respectively, one of the connecting buckles is buckled to one of the connecting necks, one of the connecting female buckles is buckled to one of the connecting sub-buckles, and the rear cover is fixed to the main body.

Preferably, at least one fixing female buckle is provided at both sides of one of the main body and the rear cover, and at least one fixing sub-buckle is provided at both sides of the other of the main body and the rear cover, one of the fixing female buckles is buckled to one of the fixing sub-buckles, and the rear cover is fixed to the main body.

Preferably, a plurality of fixing female buckles are provided at both sides of one of the main body and the rear cover, respectively, a plurality of fixing sub-buckles are provided at both sides of the other of the main body and the rear cover, the plurality of fixing female buckles are oppositely provided at both sides of the main body or the rear cover and are provided at intervals far from the connecting portion, one of the fixing female buckles is buckled to one of the fixing sub-buckles, and the rear cover is fixed to the main body.

Preferably, at least one limiting groove is provided at both sides of one of the main body and the rear cover, at least one limiting rib is provided at both sides of the other of the main body and the rear cover, one of the limiting ribs is inserted into one of the limiting grooves, and the rear cover is limited to the main body; and/or at least one positioning pin is provided in one of the main body and the rear cover, and at least one positioning slot is provided in the other of the main body and the rear cover, one of the positioning pins is inserted into one of the positioning slots, and the rear cover is positioned on the main body.

Preferably, the rear cover has an arched cross section and defines an arched cavity, at least one limiting member is provided at both sides of the main body, respectively, and each of the limiting members abuts against the wall of the inner cavity of the arched cavity when the rear cover is buckled to the main body.

Preferably, the main body comprises a middle frame and a front case, one end of the middle frame is provided with a connecting portion fixedly connected to the external load, and the other end thereof encircles an inner cavity in which an internal electronic component is installed together with the front case, the rear cover is fixedly installed to the middle frame and covers the inner cavity, the extension is provided on the middle frame, and the extension extends toward the rear cover and the front case and covers the ends of the front case and the rear cover.

Preferably, the inner cavity is further provided with at least one light source electrically connected to the electronic component, the front case is further provided with at least one light transmitting portion, and the ray of light emitted by each of the light sources is at least partially transmitted from the light transmitting portion; and/or the inner cavity is further provided with a plug terminal for the charging and data transmission of the battery assembly, the plug terminal is electrically connected to the electronic component, and the middle frame is provided with a plug port exposing the plug terminal.

The present invention further provides an electronic cigarette comprising an atomizer and a battery assembly, wherein the battery assembly comprises a main body and a rear cover fixedly installed to the main body, wherein one end of the main body is provided with a connecting portion fixedly electrically connected to an external load, and the other end thereof is provided with an inner cavity for accommodating an electronic component, the rear cover is fixedly installed to the main body and covers the inner cavity, one end of the main body far from the connecting portion is provided with an extension toward the rear cover, and the extension covers the end of the rear cover far from the connecting portion.

The battery assembly of the technical solution of the present invention is provided with an extension toward the rear cover at one end of the main body far from the connecting portion, and the extension covers the end of the rear cover far from the connecting portion. It is to be understood that during the use, the end connected to the external load is held upward. When the battery assembly drops from the user's hand, the extension provided by the main body wraps the end of the rear cover to protect the rear cover, preventing the phenomenon that an impact point or a crack is resulted from the surface collision due to the direct contact between the rear cover and the ground.

BRIEF DESCRIPTION OF THE DRAWINGS

For a better illustration of the embodiments of the present invention or the technical solution in the prior art, accompanying drawings needed in the description of the embodiments or the prior art are simply illustrated below. Obviously, the accompanying drawings described below are some embodiments of the present invention. For those skilled in the art, other accompanying drawings may be obtained according to the structure shown in these accompanying drawings without creative work.

DESCRIPTION OF THE REFERENCE NUMBERS

| Reference number | Name |
| --- | --- |
| 1000 | electronic cigarette |
| 100 | atomizer |
| 10 | main body |
| 11 | middle frame |
| 111 | connecting portion |
| 112 | inner cavity |
| 113 | extension |
| 114 | connecting neck |
| 1141 | auxiliary buckle |
| 115 | connecting sub-buckle |
| 116 | fixing sub-buckle |
| 117 | limiting groove |
| 118 | positioning slot |
| 119 | first limiting plate |
| 12 | front case |
| 30 | rear cover |
| 31 | connecting buckle |

-continued

| Reference number | Name |
| --- | --- |
| 311 | auxiliary neck |
| 32 | connecting female buckle |
| 321 | reinforcing rib |
| 322 | connecting hole |
| 33 | fixing female buckle |
| 331 | reinforcing rib |
| 332 | fixing hole |
| 34 | limiting rib |
| 35 | positioning pin |
| 36 | second limiting plate |
| 50 | electronic component |
| 51 | main control board |
| 52 | plug terminal |
| 53 | light source |
| 54 | battery |
| 55 | conductive terminal |
| 60 | triggering microphone |
| 70 | partition plate |
| 71 | installing notch |
| 80 | sealing member |
| 81 | sealing portion |
| 82 | cover portion |
| 83 | wind blocking rib |
| 84 | boss |
| 85 | air guiding groove |
| 200 | atomizer |
| 210 | heat generating core |
| 220 | oil storage chamber |
| 230 | air outlet passage |
| 240 | electrode contact |

The implementation of aims, the function features and the advantages of the present disclosure are described below in further detail in conjunction with embodiments with reference to the drawings.

DESCRIPTION OF THE EMBODIMENTS

A clear and complete description as below is provided for the technical solution in the embodiments of the present invention in conjunction with the drawings in the embodiments of the present invention. Obviously, the embodiments described hereinafter are simply part embodiments of the present invention, rather than all the embodiments. All other embodiments obtained by those skilled in the art based on the embodiments in the present invention without creative work are intended to be included in the scope of protection of the present invention.

It should be noted that all directional indications (such as top, bottom, left, right, front, behind . . . ) in the embodiments of the present invention are merely to illustrate a relative position relation, a relative motion condition, etc. between each part in a certain state (for example, the state shown in the drawings). If the state changes, the directional indication changes accordingly.

In addition, if terms "first", "second", etc. appear in the present invention, they are merely for the purpose of description, but cannot be understood as the indication or implication of relative importance or as the implicit indication of the number of the designated technical features; therefore, features defined by "first" and "second" may specifically or implicitly comprise at least one such feature. In addition, technical solutions of each embodiment of the present invention may be combined mutually; however, this must be carried out on the basis that those skilled in the art can implement the combination. When the combination of technical solutions has a conflict or cannot be implemented, it should considered that such combination of technical solutions does not exist and is not in the scope of protection claimed by the present invention.

In the present invention, unless otherwise specifically stated and defined, terms "connected", "fixed", etc. should be interpreted expansively. For example, "fixed" may be fixed connection, detachable connection, or integration; may be mechanical connection or electrical connection; direct connection, indirect connection through an intermediate, or internal communication between two elements or interaction of two elements, unless otherwise specifically defined. Those skilled in the art can understand the specific implication of the above terms in the present invention according to specific conditions.

The present invention provides a battery assembly 100 for supplying power to an external load. Here, in the present embodiment, the external load is an atomizer 200. The battery assembly 100 is combined with the atomizer 200 to form an electronic cigarette 1000. The atomizer 200 is provided with an oil storage chamber 220 and a heat generating core. The battery assembly 100 is provided with a connecting portion 111 fixedly electrically connected to the atomizer 200, and then controls the power output current through the electronic component 50 provided in the battery assembly 100 to power the heat generating core in the atomizer 200, so that the heat generating core heats the tobacco juice under the driving of the battery assembly 100 to generate smoke, and then the smoke is discharged through an air outlet for the user to smoke, thereby enabling the user to obtain a smoking experience. The battery assembly 100 is internally provided with are chargeable battery element 54 and is provided with an output terminal that can be used to charge an external terminal. The output terminal may be a USB output socket or the like.

Referring to FIG. 1 to FIG. 10, in the embodiment of the present invention, the battery assembly 100 comprises a main body 10 and a rear cover 30 fixedly installed to the main body 10, wherein one end of the main body 10 is provided with a connecting portion 111 fixedly electrically connected to an external load, and the other end thereof is provided with an inner cavity 112 for accommodating an electronic component 50, the rear cover 30 is fixedly installed to the main body 10 and covers the inner cavity 112, one end of the main body 10 far from the connecting portion 111 is provided with an extension 113 toward the rear cover 30, and the extension 113 covers the end of the rear cover 30 far from the connecting portion 111. Here, specifically, in the present embodiment, the extension 113 of the main body 10 is made of a metal material, and the rear cover 30 is prepared by an in-molding injection molding process so that the surface has various patterns.

The battery assembly 100 of the technical solution of the present invention is provided with an extension 113 toward the rear cover 30 at one end of the main body 10 far from the connecting portion 111, and the extension 113 covers the end of the rear cover 30 far from the connecting portion 111. It is to be understood that during the use, the end connected to the external load is held upward. When the battery assembly 100 drops from the user's hand, the extension 113 provided by the main body 10 wraps the end of the rear cover 30 to protect the rear cover 30, preventing the phenomenon that an impact point or a crack is resulted from the surface collision due to the direct contact between the rear cover 30 and the ground.

Figure 3:
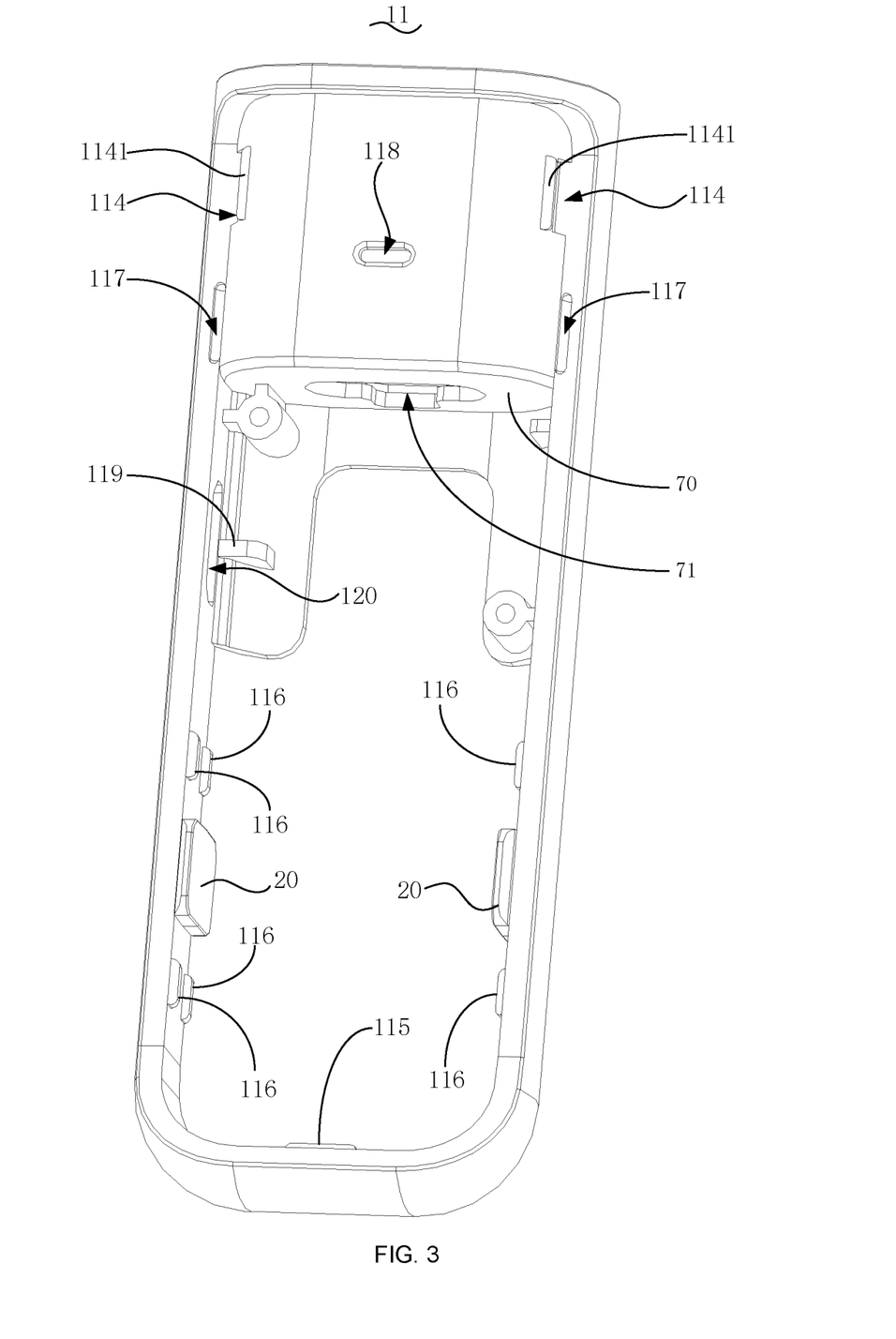
FIG. 3 is a perspective diagram illustrating a connecting structure of a middle frame in a battery assembly according to the present invention.
Figure 4:
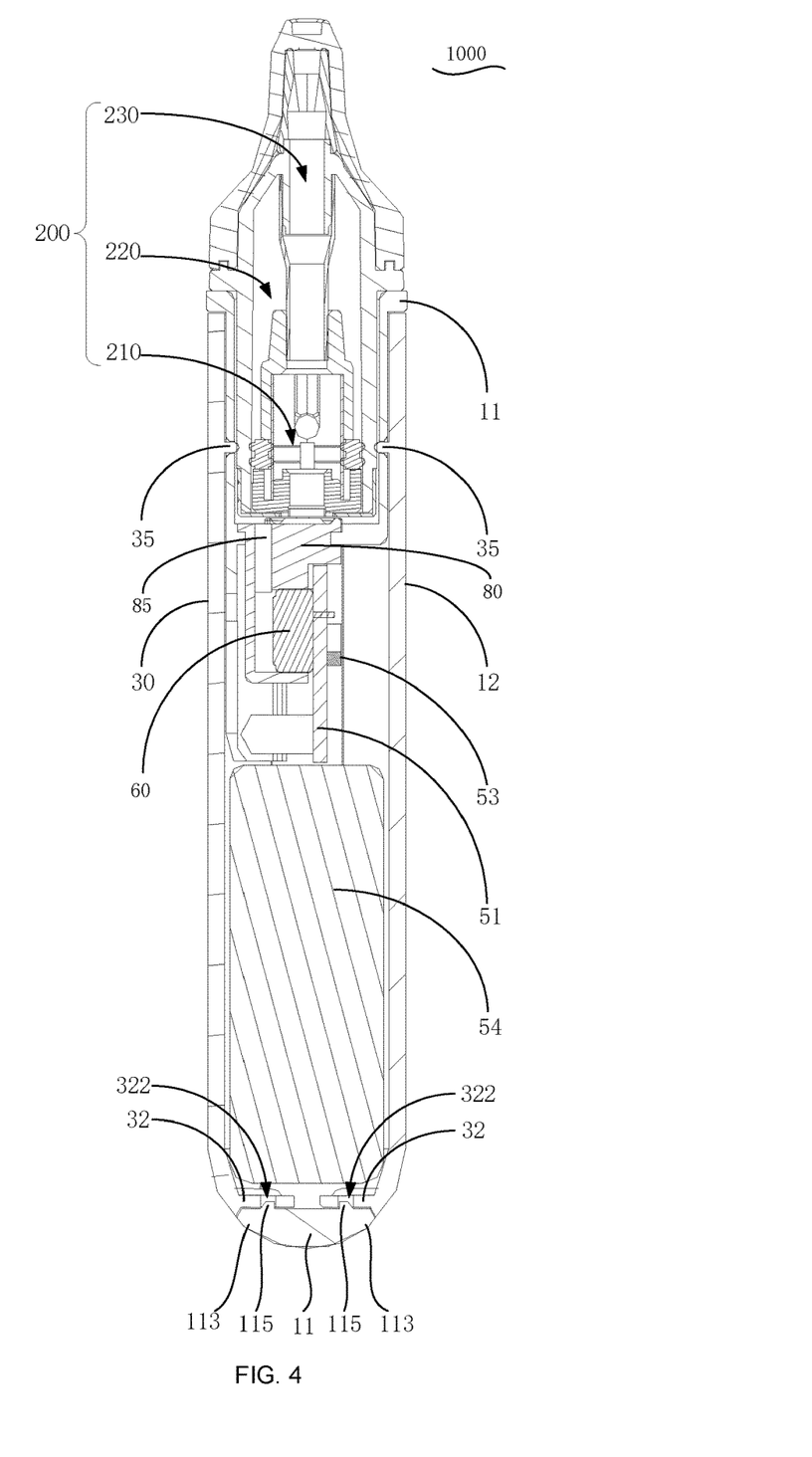
FIG. 4 is a cross-sectional diagram illustrating a connecting structure of an electronic cigarette according to the present invention.
Figure 5:
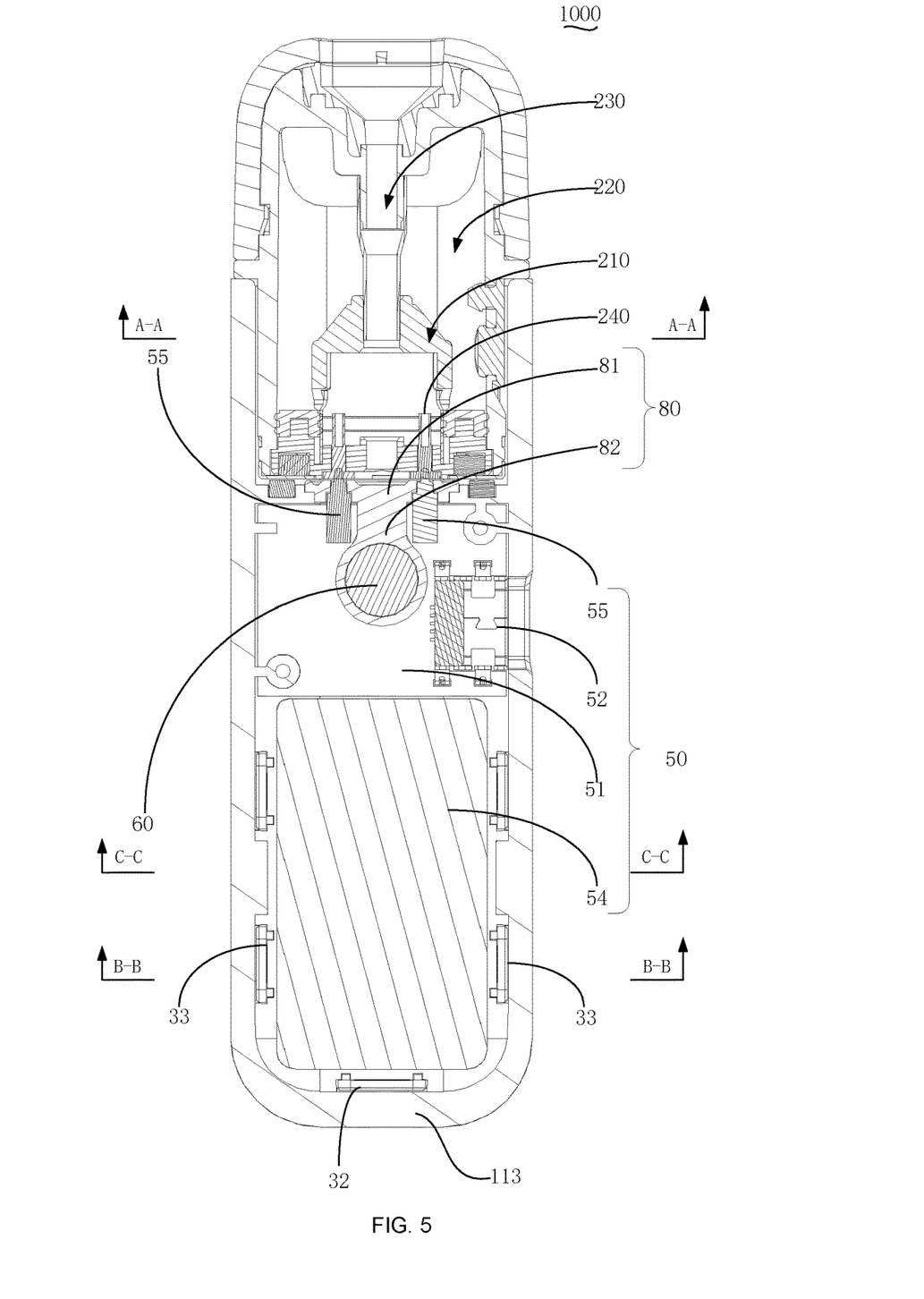
FIG. 5 is a cross-sectional diagram illustrating a connecting structure of an electronic cigarette according to the present invention when viewed from another direction.

Specifically, as shown in FIG. 3 to FIG. 5, in the embodiment of the present invention, the rear cover 30 and the extension 113 far from one end of the connecting portion 111 are integrally connected in a curved smooth transition manner. Here, the electronic component 50 is provided at one end of the inner cavity 112 near the extension 113, so that the entire center of gravity of the battery assembly 100 is shifted to be close to the extension 113. Moreover, due to the center of gravity, when the battery assembly 100 is dropped, the probability that the extension 113 is in direct contact with the ground is increased. The rear cover 30 and the extension 113 far from one end of the connecting portion 111 are integrally provided in a hemispherical curved surface, so that the side structure has no protruding edges and corners. When the battery assembly 100 is dropped, the extension 113 of the curved surface is in contact with the ground, and the impact force is easily diffused, thereby avoiding the occurrence of hard collision damage of the edges and corners.

Figure 1:
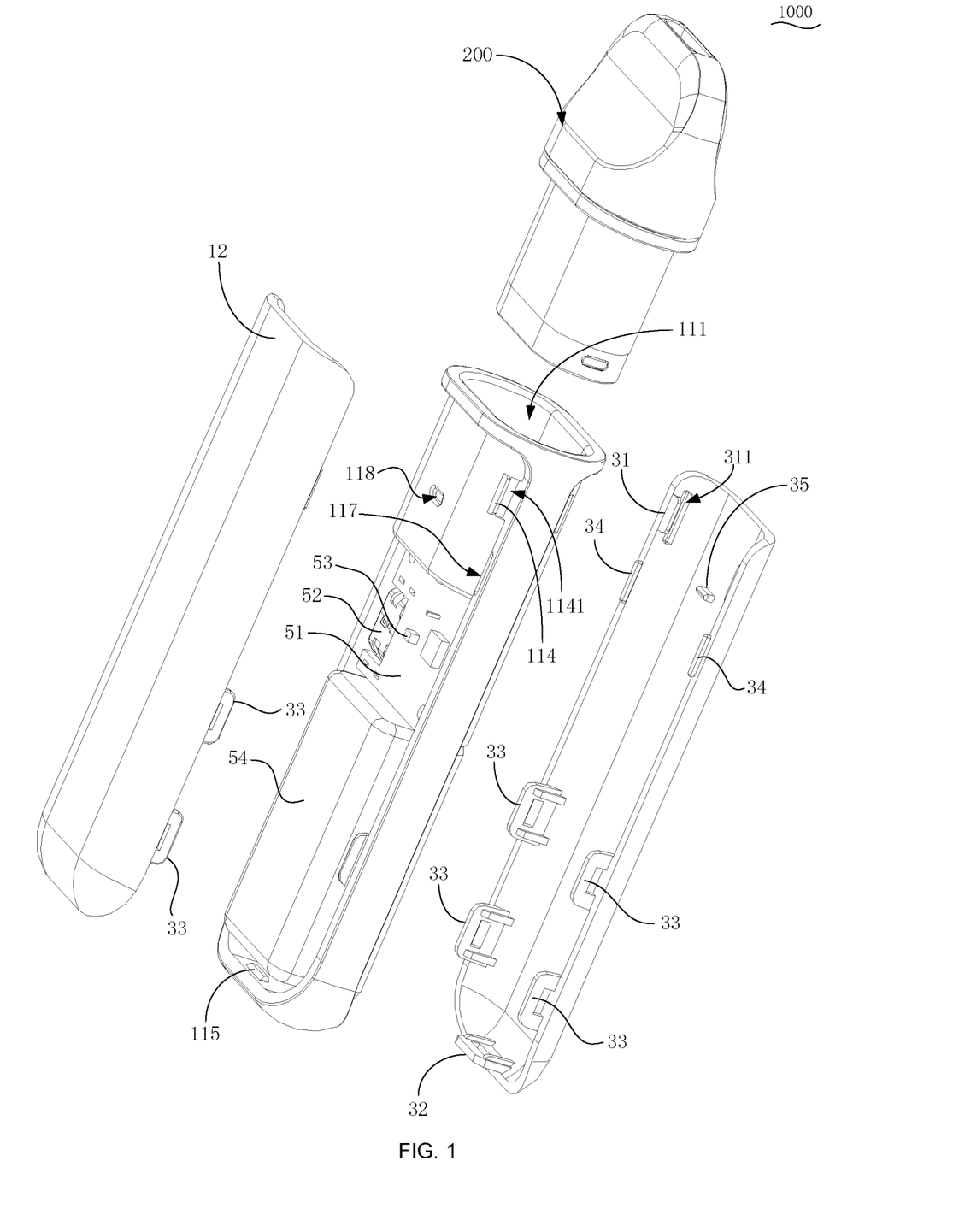
FIG. 1 is a schematic exploded diagram illustrating a connecting structure of an electronic cigarette according to the present invention.
Figure 2:
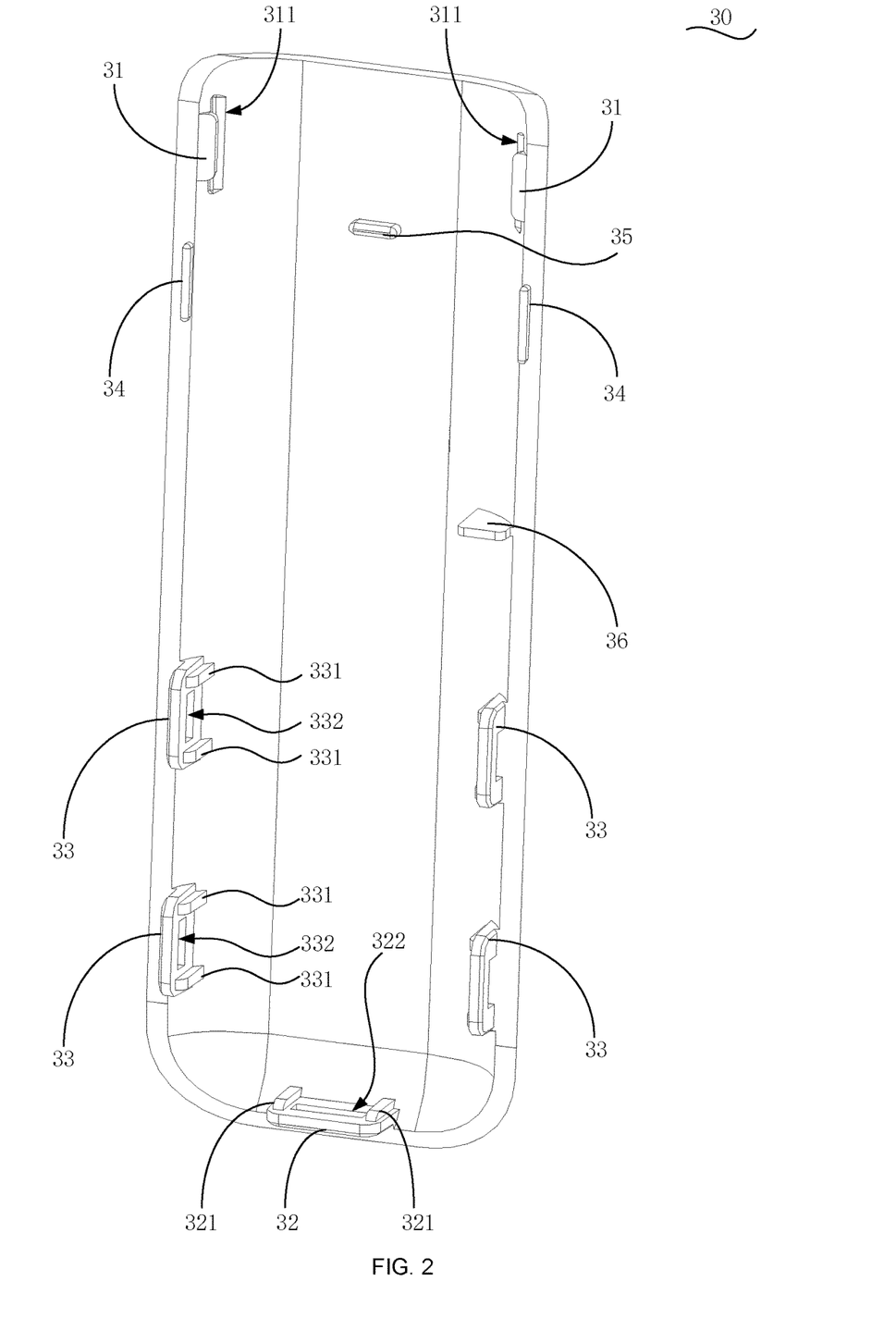
FIG. 2 is a perspective diagram illustrating a connecting structure of a rear cover in a battery assembly according to the present invention.

Specifically, as shown in FIG. 1 to FIG. 3, in the embodiment of the present invention, at least one connecting buckle 31 and at least one connecting female buckle 32 are provided at both ends of one of the main body 10 and the rear cover 30, respectively, at least one connecting neck 114 and at least one connecting sub-buckle 115 are correspondingly provided at both ends of the other of the main body 10 and the rear cover 30, respectively, one of the connecting buckles 31 is buckled to one of the connecting necks 114, one of the connecting female buckles 32 is buckled to one of the connecting sub-buckles 115, and the rear cover 30 is fixed to the main body 10. Here, in the present embodiment, one end of the main body 10 near the connecting portion 111 is provided with two connecting necks 114, and one end of the main body far from the connecting portion 111 is provided with a connecting sub-buckle 115. The two connecting necks 114 are oppositely provided at both sides of the main body 10 at intervals. Two connecting buckles 31 and a connecting female buckle 32 are correspondingly provided at both sides of the rear cover 30, the two connecting buckles 31 are buckled to the two connecting necks 114, respectively, one of the connecting female buckles 32 is buckled to one of the connecting sub-buckles 115, the rear cover 30 is fixed to the main body 10, and the connection is stable. When the battery assembly 100 is dropped, the connecting buckles 31 provided laterally at intervals limit the shake of the rear cover 30 in the lateral direction. The connecting female buckle 32 limits the shake of the rear cover 30 in the longitudinal direction, thereby effectively preventing the phenomenon that the rear cover 30 is detached from the main body 10 due to the impact so as to cause damage to the internal electronic component 50.

It is to be understood that, in actual application, the number of the connecting buckles 31 and the connecting female buckles 32 is designed according to the actual product size. At the same time, the connecting buckles 31 and the connecting female buckles 32 are not limited to the above manner of being provided on the rear cover 30. For example, the manner, in which the connecting sub-buckles 115 and the connecting necks 114 are further correspondingly provided for fixing in such a way that the connecting buckle 31 and the connecting female buckle 32 may be provided on the main body 10, or the connecting buckle 31 may be provided on the main body 10 and the connecting female buckle 32 may be provided on the rear cover 30, also falls within the scope of protection of the present invention.

Specifically, as shown in FIG. 2, in the embodiment of the present invention, the connecting female buckle 32 is provided with a connecting hole 322. When the connecting female buckle 32 is buckled to the connecting sub-buckle 115, the connecting sub-buckle 115 is inserted into the connecting hole 322 for fixing, which effectively prevents the phenomenon that the connecting sub-buckle 115 is detached from the connecting female buckle 32, and enhances the stability of connecting the rear cover 30 and the main body 10.

Specifically, as shown in FIG. 2, in the embodiment of the present invention, the connecting female buckle 32 is convexly provided with two reinforcing ribs 331 to be fixedly connected with the rear cover 30 adjacent to the connecting hole 322, which effectively enhances the strength of connecting the connecting female buckle 32 and the rear cover 30 and prevents the connecting female buckle 32 from being broken.

Figure 6:
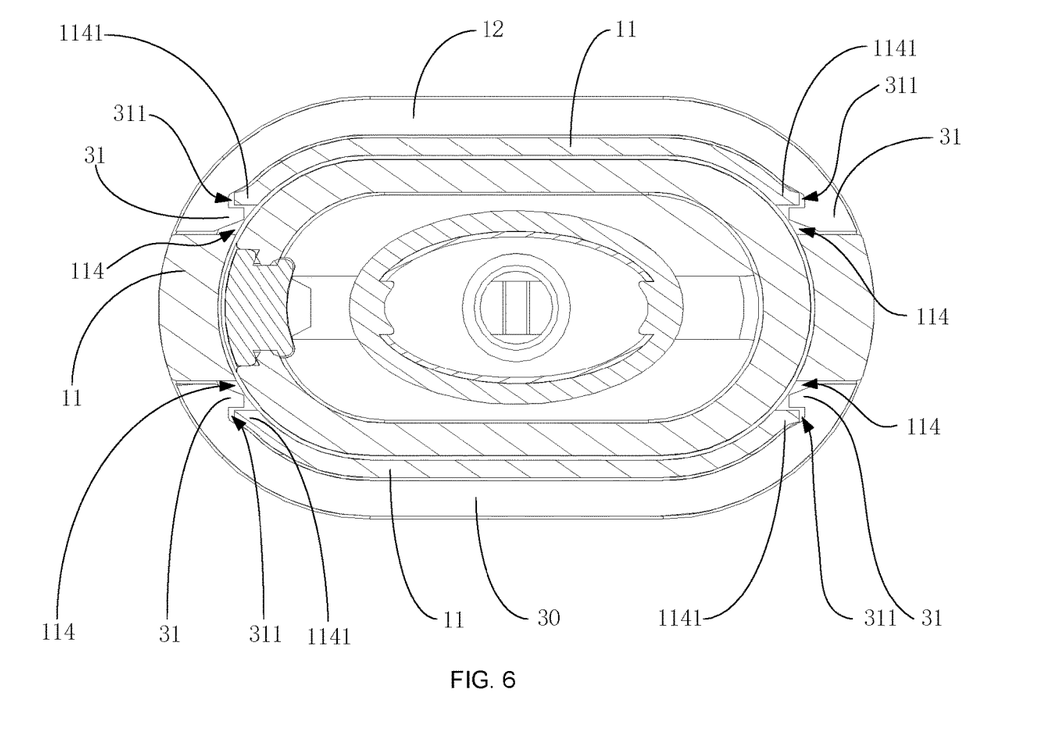
FIG. 6 is a cross-sectional diagram taken along line A-A of FIG. 5 according to the present invention.

Further, as shown in FIG. 1 or FIG. 3 or FIG. 6, in the embodiment of the present invention, the main body 10 is further provided with an auxiliary buckle 1141 adjacent to each of the connecting necks 114. The inner side of the rear cover 30 is further provided with an auxiliary neck 311 adjacent to each of the connecting buckles 31. When one of the connecting buckles 31 is buckled to one of the connecting necks 114, one of the auxiliary buckles 1141 is inserted into one of the auxiliary necks 311 to form a cross-buckling form. When the connecting buckle 31 has a tendency to be detached from the connecting neck 114 by an external impact force, the auxiliary buckle 1141 has a resisting force against the connecting buckle 31, which prevents the phenomenon that the connecting buckle 31 is detached from the connecting neck 114, and further enhances the stability of connecting the rear cover 30 and the connecting neck 114.

Further, as shown in FIG. 1 or FIG. 2, in the embodiment of the present invention, at least one fixing female buckle 33 is provided at both sides of one of the main body 10 and the rear cover 30, and at least one fixing sub-buckle 116 is provided at both sides of the other of the main body 10 and the rear cover 30, one of the fixing female buckles 33 is buckled to one of the fixing sub-buckles 116, and the rear cover 30 is fixed to the main body 10. Here, in the present embodiment, one fixing sub-buckle 116 is provided at both sides of the main body 10. A fixing female buckle 33 is correspondingly provided at both sides of the rear cover 30, respectively. One of the fixing female buckles 33 is buckled to one of the fixing sub-buckles 116, which further prevents the phenomenon that the rear cover 30 is detached from the main body 10 by an external impact force.

Specifically, as shown in FIG. 1 to FIG. 3, in the embodiment of the present invention, a plurality of fixing female buckles 33 are provided at both sides of one of the main body 10 and the rear cover 30, respectively, a plurality of fixing sub-buckles 116 are provided at both sides of the other of the main body 10 and the rear cover 30, the plurality of fixing female buckles 33 are oppositely provided at both sides of the main body 10 or the rear cover 30 and are provided at intervals far from the connecting portion 111, one of the fixing female buckles 33 is buckled to one of the fixing sub-buckles 116, and the rear cover 30 is fixed to the main body 10. Here, in the present embodiment, two fixing buckles 116 are provided at both sides of the main body 10 far from the one end of the connecting portion 111, two fixing female buckles 33 are correspondingly provided at both sides of the rear cover 30, respectively, and one of the fixing female buckles 33 is buckled to one of the fixing sub-buckles 116, which effectively enhances the stability of connecting the main body 10 and the rear cover 30 adjacent to one end of the center of gravity and further prevents the phenomenon that the rear cover 30 is detached from the main body 10 by an external impact force.

Figure 7:
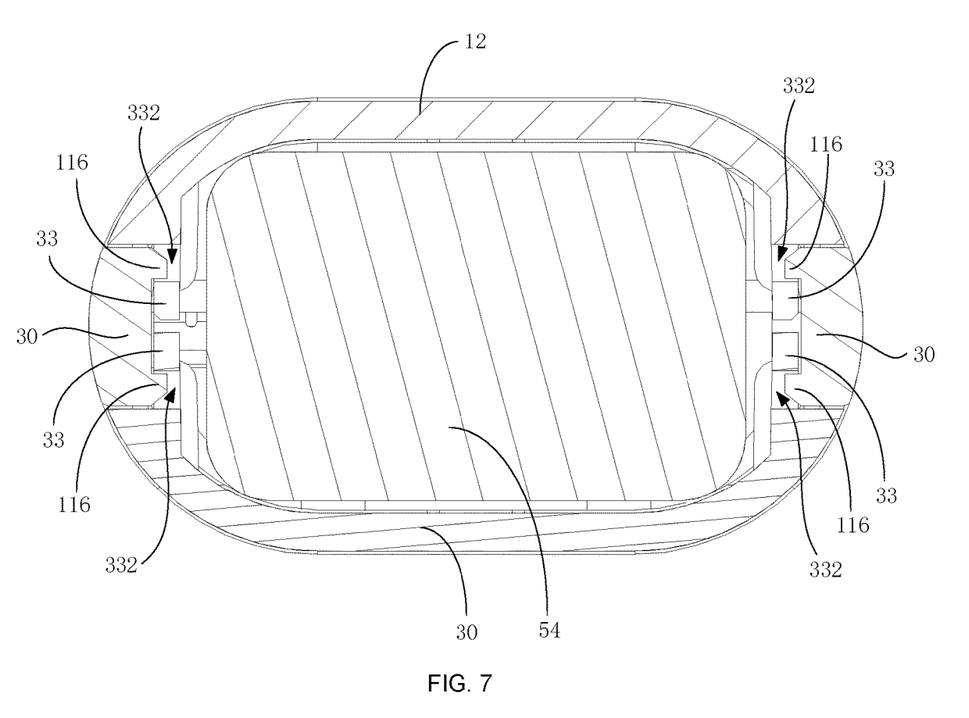
FIG. 7 is a cross-sectional diagram taken along line B-B of FIG. 5 according to the present invention.

Specifically, as shown in FIG. 2 and FIG. 7, in the embodiment of the present invention, each of the fixing female buckles 33 is provided with a fixing hole 332. When the fixing female buckle 33 is buckled to the fixing sub-buckle 116, the fixing sub-buckle 116 is inserted into the fixing hole 332 for fixing, which effectively prevents the phenomenon that the fixing sub-buckle 116 is detached from the fixing female buckle 33 and further enhances the stability of connecting the rear cover 30 and the main body 10.

Specifically, as shown in FIG. 2, in the embodiment of the present invention, the fixing female buckle 33 is further convexly provided with two reinforcing ribs 321 to be fixedly connected to the rear cover 30 adjacent to the fixing hole 332, which effectively enhances the strength of connecting the fixing female buckle 33 and the rear cover 30 and prevents the fixing female buckle 33 from being broken.

Further, as shown in FIG. 2 and FIG. 3, in the embodiment of the present invention, at least one limiting groove 117 is provided at both sides of one of the main body 10 and the rear cover 30, at least one limiting rib 34 is provided at both sides of the other of the main body 10 and the rear cover 30, one of the limiting ribs 34 is inserted into one of the limiting grooves 117, and the rear cover 30 is limited to the main body 10; here, in the present embodiment, a limiting groove 117 is provided at one end of the main body 10 adjacent to the connecting portion 111. The limiting ribs 34 are correspondingly provided at both sides of the rear cover 30. When the rear cover 30 is buckled to the main body 10, one of the limiting ribs 34 is inserted into one of the limiting grooves 117, which effectively prevents the lateral shake when the rear cover 30 is subjected to an impact force, and further prevents the phenomenon that the rear cover 30 is detached from the main body 10 due to the external impact force. At the same time, it has a positioning effect during installation, which is convenient for the user to install.

Further, as shown in FIG. 2 and FIG. 3, in the embodiment of the present invention, at least one positioning pin 35 is provided in one of the main body 10 and the rear cover 30, and at least one positioning slot 118 is provided in the other of the main body 10 and the rear cover 30, one of the positioning pins 35 is inserted into one of the positioning slots 118, and the rear cover 30 is positioned on the main body 10. Here, in the present embodiment, the main body 10 is provided with a positioning slot 118, and the rear cover 30 is convexly provided with a positioning pin 35. When the rear cover 30 is buckled to the main body 10, the positioning pin 35 is inserted into the positioning slot 118. When the rear cover 30 is impacted, the positioning slot 118 limits the positioning pin 35, which effectively prevents the rear cover 30 from shaking laterally or longitudinally, and further prevents the phenomenon that the rear cover 30 is detached from the main body 10 due to the external impact force. At the same time, it has a positioning effect during installation, which is convenient for the user to install.

Figure 8:
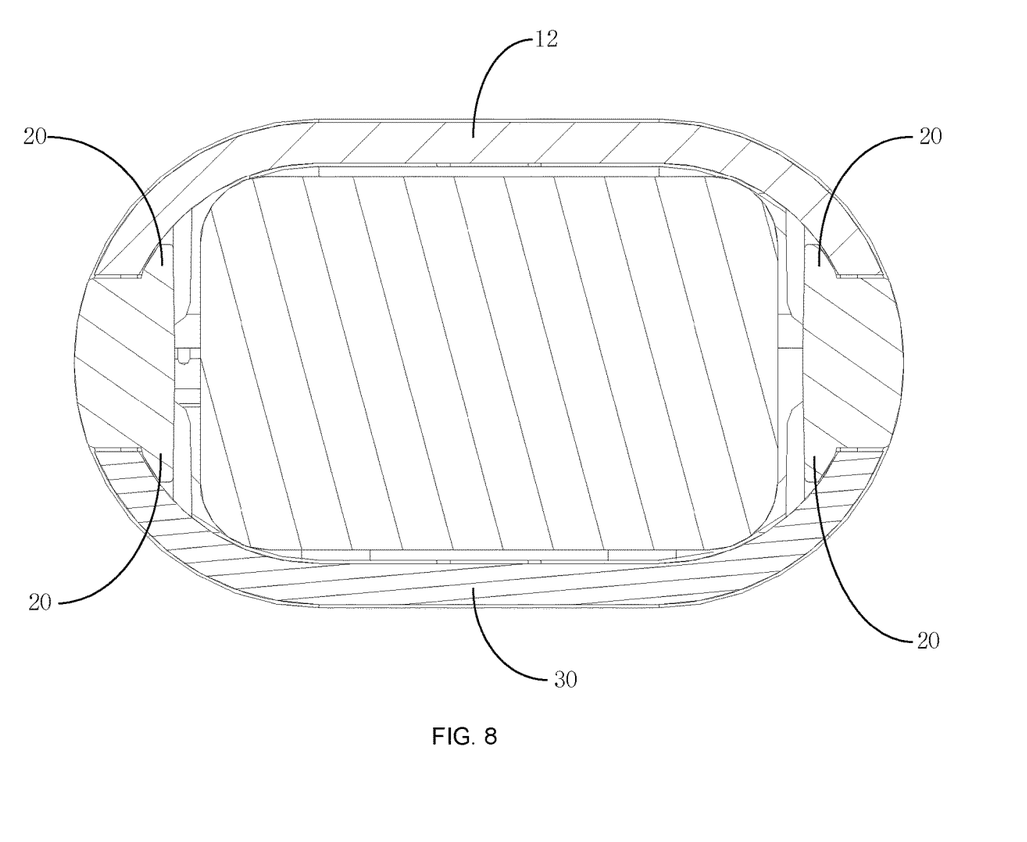
FIG. 8 is a cross-sectional diagram taken along line C-C of FIG. 5 according to the present invention.

Specifically, as shown in FIG. 8, in the embodiment of the present invention, the rear cover 30 has an arched cross section and defines an arched cavity, at least one limiting member is provided at both sides of the main body 10, respectively, and each of the limiting members abuts against the wall of the inner cavity 112 of the arched cavity when the rear cover 30 is buckled to the main body 10. Here, in the present embodiment, the rear cover 30 has an arched cross section, and both sides of the rear cover close to the edge are in transition connection with the main body 10 in an arched shape, thereby effectively reducing the damage caused by the collision. At the same time, a limiting member is provided at both sides of the main body 10. The limiting member is inserted into the arched cavity and adapts to abut against the wall of the inner cavity 112 of the arched cavity, which effectively enhances the connection strength. When the battery assembly 100 is dropped, the collision force is transmitted to the main body 10 by the two limiting members to be dispersed and eliminated, thereby further preventing the phenomenon that the rear cover 30 is detached from the main body 10 so as to cause damage to the internal electronic component 50.

Specifically, as shown in FIG. 1, in the embodiment of the present invention, the main body 10 comprises a middle frame 11 and a front case 12, one end of the middle frame 11 is provided with a connecting portion 111 fixedly connected to the external load, and the other end thereof encircles an inner cavity 112 in which an internal electronic component 50 is installed together with the front case 12, the rear cover 30 is fixedly installed to the middle frame 11 and covers the inner cavity 112, the extension 113 is provided on the middle frame 11, and the extension 113 extends toward the rear cover 30 and the front case 12 and covers the ends of the front case 12 and the rear cover 30. Here, in the present embodiment, the middle frame 11 is made of a metal material, the front case 12 and the rear cover 30 are identical in structure, and the specific connecting structure of the front case 12 and the middle frame 11 is as described above with reference to the embodiment. Due to the use of all the technical solutions of all the above embodiments, the front cover and the middle frame 11 have at least all the beneficial effects brought by the technical solutions of the above embodiments, which will not be described in detail herein.

Figure 9:
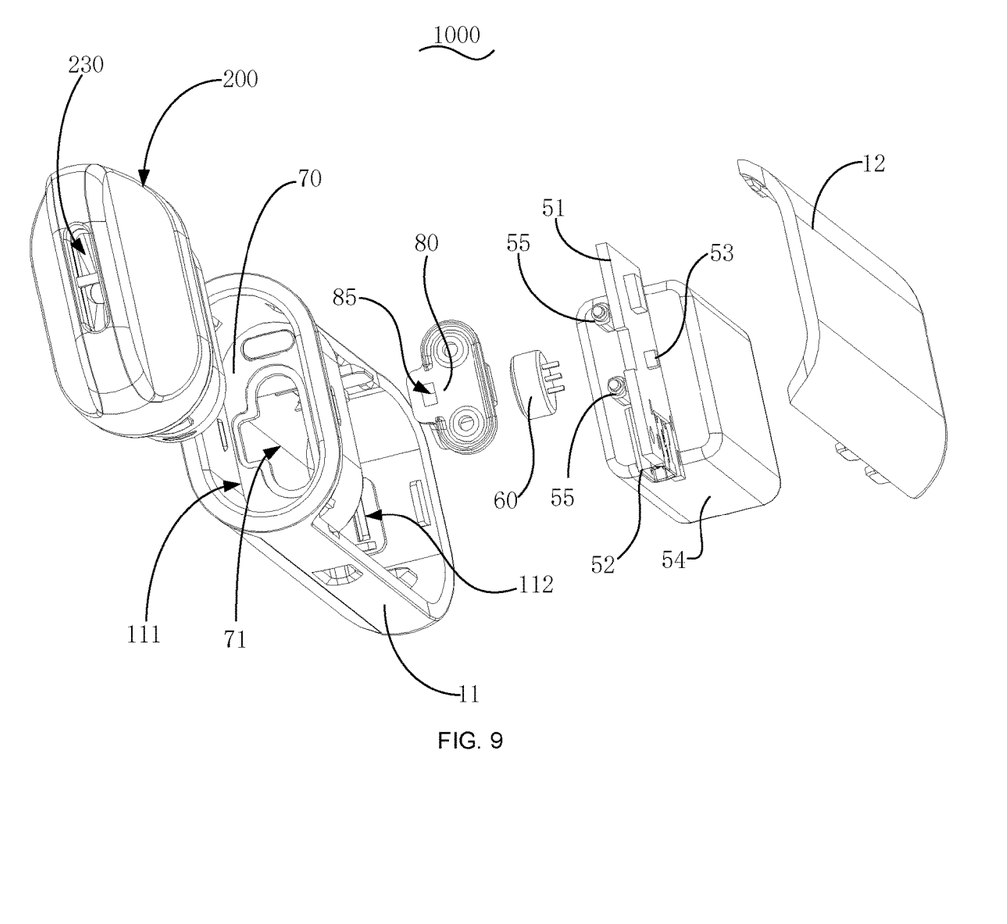
FIG. 9 is another schematic exploded diagram illustrating a connecting structure of an electronic cigarette according to the present invention.

Further, as shown in FIG. 1 or FIG. 9, in the embodiment of the present invention, the inner cavity 112 is further provided with at least one light source 53 electrically connected to the electronic component 50, the front case 12 is further provided with at least one light transmitting portion, and the ray of light emitted by each of the light sources 53 is at least partially transmitted from the light transmitting portion; here, in the present embodiment, the electronic component 50 comprises a main control board 51 and a battery 51 electrically connected to the main control board 51. The light source 53 is an LED lamp bead. Each of the LED lamp bead is integrated in the main control board 51. The light transmitting portion has various patterns formed by the front cover using the In Molding Label process. A circular hole may also be formed as a function indicator light, or the form such as an empty groove communicated with the outside may be used.

It is to be understood that, in actual application, there may be provided with a plurality of light sources 53, the plurality of light sources 53 have a common electrode terminal and are electrically connected in parallel to effectively facilitate wiring, and when a single LED lamp bead is damaged, other LED lamp beads can operate normally without affecting the overall working state; at the same time, each of the light sources 53 is not limited to the above connection manner of being electrically integrated in the main control board 51. For example, the manner, in which a conductive member or a flexible circuit board may be electrically connected with main control board 51, also falls within the scope of protection of the present invention.

Further, manner, in which those skilled in the art can also adjust the illumination intensity, stroboscopic, and color conversion of the LED lamp bead by adding a PWM circuit module (not shown) on the main control board 51 to achieve various types of light effects, also falls within the scope of protection of the present invention.

Further, as shown in FIG. 5, in the embodiment of the present invention, the inner cavity 112 is further provided with a plug terminal 52 for the charging and data transmission of the battery assembly 100, the plug terminal 52 is electrically connected to the electronic component 50, and the middle frame 11 is provided with a plug port exposing the plug terminal 52. Here, in the present embodiment, the plug terminal 52 may be a micro jack, a lighting jack, or a Type c jack. At the same time, the middle frame 11 is provided with a first limiting plate 119. The rear cover 30 is provided with a second limiting plate 36. The first limiting plate 119 and the second limiting plate abut against the outer periphery of the plug terminal 52, respectively, to limit the plug terminal 52, which effectively prevents the plug terminal 52 from shaking and avoids the phenomenon that the plugging terminal 52 is damaged by excessive force when the user plugs.

Referring to FIG. 1, FIG. 4 or FIG. 5, the present invention further provides an electronic cigarette 1000. The electronic cigarette 1000 comprises an atomizer 200 and a battery assembly 100. Refer to the above embodiment for the specific structure of the battery assembly 100. Due to the use of all the technical solutions of all the above embodiments, the electronic cigarette 1000 has at least all the beneficial effects brought by the technical solutions of the above embodiments, which will not be described in detail herein.

The atomizer 200 comprises a housing, a base, and a heat generating core 210. The base and the housing encircle an oil storage chamber 220. The heat generating core 210 is provided in the oil storage chamber 220 and is communicated with the oil storage chamber 220. The base is provided with an air inlet communicated with the heat generating core 210. The heat generating core 210 is provided with an air outlet passage 230 communicated with the outside for the user to smoke, and the heat generating core 210 is electrically connected to the battery assembly 100 when the atomizer 200 is installed to the connecting portion 111.

Specifically, as shown in FIG. 5, in the embodiment of the present invention, the heat generating core 210 comprises a heat generating body and two electrode contacts 240 electrically connected to the heat generating body. The two electrode contacts 240 are exposed to the outside through the base. The inner wall of the middle frame 11 is convexly provided with a partition plate 70 to partition the inner space of the middle frame 11 into an installing cavity for installing the atomizer 200 and an inner cavity 112 for accommodating the internal electronic component 50. The bottom cavity wall of the installing cavity is provided with an installing notch 71 communicated with the inner cavity 112. The battery assembly 100 is further provided with a sealing member 80. The sealing member 80 is sealingly provided around the installing notch 71. The main control board 51 is further electrically connected to two elastic thimbles. The two elastic thimbles are exposed to the installing cavity through the sealing member 80 to form a connecting portion 111. When one end of the atomizer 200 is inserted into the installing cavity, the two electrode contacts 240 elastically abut against the two elastic thimbles to form an electrical circuit. Here, the inner wall of the middle frame 11 is convexly provided with a partition plate 70 to partition the main body 10 into an installing cavity and an inner cavity 112 for accommodating the internal electronic component 50, since the partition plate 70 is integrally formed with the middle frame 11 to form a cup. The sealing member 80 is sealingly provided around the installing notch 71, which effectively prevents oil from penetrating into the inner cavity 112 from the gap between the partition plate 70 and the main body 10 or from the installing notch 71 to cause damage to the internal electronic component 50. At the same time, the rear cover 30 is pressed against the main body 10 and covers the inner cavity 112. When the internal components are faulty, only the rear cover 30 needs to be removed for maintenance without moving the sealing member 80, thereby effectively preventing the phenomenon that in the process of multiple disassembly and assembly of the conventional small-sized electronic cigarette 1000, the sealing member 80 is enclosed into the sleeve with the skeleton so as to easily result in turnup and gaps so that the tobacco juice in the atomizer 200 is easily leaked into the inner cavity 112 and damages the electronic component 50, and effectively enhancing the sealing effect of the battery assembly 100.

It is to be understood that, in the actual application, the connecting portion 111 is not limited to the above form in which the two elastic thimbles pass through the sealing member 80. For example, the manner, in which a negative electrode large copper member and a positive electrode elastic conductive column are provided, the negative electrode large copper member is provided with a threaded hole to be fixedly connected with the atomizer 200, the positive electrode elastic conductive column is fixedly installed in the threaded through hole and is spaced from the threaded through hole to form positive and negative electrode contacts, also falls within the scope of protection of the present invention.

Figure 10:
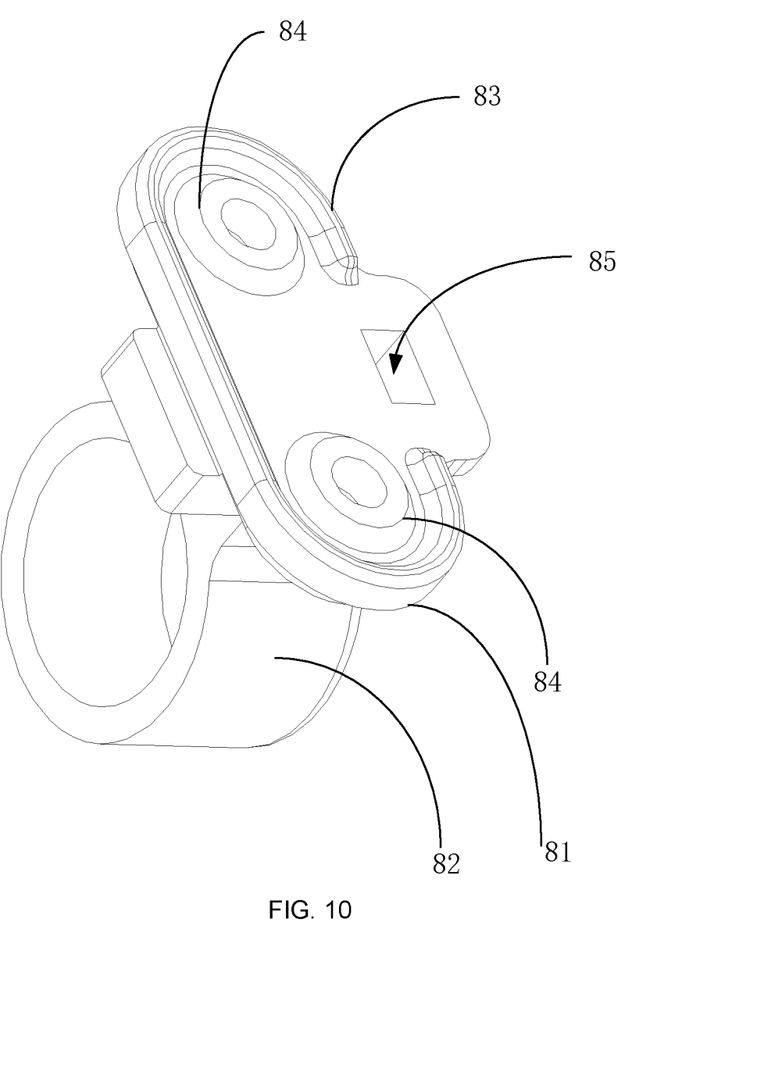
FIG. 10 is a perspective diagram illustrating a connecting structure of a sealing member in a battery assembly according to the present invention.

Further, as shown in FIG. 10, in the embodiment of the present invention, one end of the sealing member 80 toward the installing cavity is further provided with a boss 84 around each of the conductive terminals 55; here, in the present embodiment, the large-diameter end of the sealing member 80 is further provided with a boss 84 around each of the conductive terminals 55, which effectively prevents the safety hazard that the condensed water or the tobacco juice leaked from the air inlet end of the atomizer 200 converges to directly enable the two conductive terminals 55 to be conducted to result in the short circuit, and effectively improves the safety performance of the battery assembly 100.

Specifically, as shown in FIG. 5, in the embodiment of the present invention, when one end of the atomizer 200 is inserted into the installing cavity, an intake passage communicated with the outside air is formed between the housing and the base and the inner cavity 112 wall of the installing cavity. The battery assembly 100 is further provided with a triggering microphone 60 electrically connected to the electronic component 50 in the inner cavity 112. The triggering microphone 60 triggers the battery assembly 100 to supply power to the atomizer 200 when airflow in the intake passage flows at a high speed. Here, in the present embodiment, the triggering microphone 60 adopts a S087 negative pressure gas sensor switch and is integrated into the main control board 51 through a SOT-23-5 package. When the user smokes, the outside airflow flows from the gap between the atomizer 200 and the battery assembly 100, and then passes through the intake passage, and the airflow flowing at a high speed generates a negative pressure phenomenon, thereby triggering the negative pressure gas sensor switch to transmit a control signal to the battery assembly 100 and controlling the atomizer 200 to atomize the tobacco juice. At the same time, the outside airflow flows from the intake passage into the inlet end of the atomizer 200 and is atomized and mixed with the tobacco juice for the user to suck. Here, the S087 negative pressure gas sensor switch is used, the detecting accuracy is −400 pa, the triggering sensitivity is high, the quiescent current is less than 5 uA in the power-saving mode, the peripheral application circuit is simple, the volume is small, and the cost is low.

It is to be understood that, in the actual application process, the manner, in which those skilled in the art can select other types of triggering microphones 60 or simply replace them with other sensors for triggering to achieve the above beneficial effects, also falls within the scope of protection of the present invention.

Specifically, as shown in FIG. 5, in the embodiment of the present invention, the sealing member 80 comprises a sealing portion 81 and a cover portion 82. The sealing portion 81 is fixedly installed to the installing notch 71. The cover portion 82 covers the triggering microphone 60, and is provided with an air guiding groove 85 that communicates the triggering microphone 60 with the intake passage. Here, in the present embodiment, one end of the sealing member 80 is installed to the installing notch 71, and the other end thereof further extends and is provided with a cover portion 82. The cover portion 82 covers the triggering microphone to form a sealing cavity, and then an air guiding groove 85 is provided to communicate the sealing cavity with the intake passage. When the user smokes, it is to be understood that the negative pressure phenomenon formed after the gas in the narrow space in the sealing cavity is extracted is more obvious, thereby improving the triggering sensitivity, and effectively preventing the phenomenon that when the user smokes, the negative pressure value generated in the intake passage does not reach the triggering threshold of the triggering microphone 60 so that the battery assembly 100 does not supply power to the atomizer 200.

Further, as shown in FIG. 10, in the embodiment of the present invention, the large-diameter end of the sealing member 80 is further convexly provided with a wind blocking rib 83 toward the intake passage. The wind blocking rib 83 encircles an air guiding space, which is in communication with the intake passage and the air guiding groove 85. Here, in the present embodiment, the wind blocking rib 83 is provided so that when the atomizer 200 is inserted into the installing cavity, the wind blocking rib 83 convexly provided encircles an air guiding space communicated with the inlet end of the atomizer 200. The air guiding space is communicated with the intake passage to ensure an air source. The air guiding groove 85 may be provided in the air guiding space. When the user smokes, the air in the sealing cavity is preferentially extracted through the air guiding groove 85, thereby generating a negative pressure to trigger the triggering microphone 60, further improving the triggering sensitivity, and effectively preventing the phenomenon that when the user smokes, the amount of intake air around the intake passage is larger and the amount of gas extracted from the sealing cavity is smaller, so that the generated negative pressure value does not reach the triggering threshold of the triggering microphone 60 so that the battery assembly 100 does not supply power to the atomizer 200.

It is to be understood that, in actual application, the air guiding groove 85 is not limited to being provided in the air guiding space in the above embodiment. For example, in another embodiment of the present invention, the manner, in which the air guiding groove 85 may also be provided adjacent to the air guiding space, and the wind blocking rib 83 is provided with an opening adjacent to the air guiding groove 85 so that the air in the sealing cavity is easily extracted to form a negative pressure to enhance the triggering sensitivity, also falls within the scope of protection of the present invention. At the same time, the air guiding groove 85 is provided adjacent to the air guiding space, so that the air guiding groove 85 and the air inlet end of the atomizer 200 are provided in a staggered manner to prevent the phenomenon that the tobacco juice and the condensed liquid of the atomizer 200 drop into the air guiding groove 85 so as to enter the sealing cavity and damage the triggering microphone 60.

The above are preferred embodiments of the present invention merely and are not intended to limit the patent scope of protection of the present invention. Any equivalent structures made according to the description and the accompanying drawings of the present invention without departing from the idea of the present invention, or any equivalent structures applied in other relevant technical fields directly or indirectly are intended to be included in the patent scope of protection of the present invention.

What is claimed is:

1. A battery assembly, comprising: a main body and a rear cover fixedly installed to the main body, wherein one end of the main body is provided with a connecting portion fixedly electrically connected to an external load, and the other end thereof is provided with an inner cavity for accommodating an electronic component, the rear cover is fixedly installed to the main body and covers the inner cavity, one end of the main body far from the connecting portion is provided with an extension toward the rear cover, and the extension covers the end of the rear cover far from the connecting portion.

2. The battery assembly according to claim 1, wherein the rear cover and the extension far from one end of the connecting portion are integrally connected in a curved smooth transition manner.

3. The battery assembly according to claim 1, wherein the main body comprises a middle frame and a front case, one end of the middle frame is provided with a connecting portion fixedly connected to the external load, and the other end thereof encircles an inner cavity in which an internal electronic component is installed together with the front case, the rear cover is fixedly installed to the middle frame and covers the inner cavity, the extension is provided on the middle frame, the extension extends toward the rear cover and the front case, and covers the ends of the front case and the rear cover.

4. The battery assembly according to claim 3, wherein the inner cavity is further provided with at least one light source electrically connected to the electronic component, the front case is further provided with at least one light transmitting portion, and the ray of light emitted by each of the light sources is at least partially transmitted from the light transmitting portion; and/or the inner cavity is further provided with a plug terminal for the charging and data transmission of the battery assembly, the plug terminal is electrically connected to the electronic component, and the middle frame is provided with a plug port exposing the plug terminal.

5. The battery assembly according to claim 1, wherein at least one connecting buckle and at least one connecting female buckle are provided at both ends of one of the main body and the rear cover, respectively, at least one connecting neck and at least one connecting sub-buckle are correspondingly provided at both ends of the other of the main body and the rear cover, respectively, one of the connecting buckles is buckled to one of the connecting necks, one of the connecting female buckles is buckled to one of the connecting sub-buckles, and the rear cover is fixed to the main body.

6. The battery assembly according to claim 5, wherein at least one fixing female buckle is provided at both sides of one of the main body and the rear cover, and at least one fixing sub-buckle is provided at both sides of the other of the main body and the rear cover, one of the fixing female buckles is buckled to one of the fixing sub-buckles, and the rear cover is fixed to the main body.

7. The battery assembly according to claim 5, wherein a plurality of fixing female buckles are provided at both sides of one of the main body and the rear cover, respectively, a plurality of fixing sub-buckles are provided at both sides of the other of the main body and the rear cover, the plurality of fixing female buckles are oppositely provided at both sides of the main body or the rear cover and are provided at intervals away from the connecting portion, one of the fixing female buckles is buckled to one of the fixing sub-buckles, and the rear cover is fixed to the main body.

8. The battery assembly according to claim 5, wherein at least one limiting groove is provided at both sides of one of the main body and the rear cover, at least one limiting rib is provided at both sides of the other of the main body and the rear cover, one of the limiting ribs is inserted into one of the limiting grooves, and the rear cover is limited to the main body; and/or at least one positioning pin is provided in one of the main body and the rear cover, and at least one positioning slot is provided in the other of the main body and the rear cover, one of the positioning pins is inserted into one of the positioning slots, and the rear cover is positioned on the main body.

9. The battery assembly according to claim 5, wherein the rear cover has an arched cross section and defines an arched cavity, at least one limiting member is provided at both sides of the main body, respectively, and each of the limiting members abuts against the wall of the inner cavity of the arched cavity when the rear cover is buckled to the main body.

10. An electronic cigarette, comprising an atomizer, wherein the electronic cigarette further comprises the battery assembly, comprising: a main body and a rear cover fixedly installed to the main body, wherein one end of the main body is provided with a connecting portion fixedly electrically connected to an external load, and the other end thereof is provided with an inner cavity for accommodating an electronic component, the rear cover is fixedly installed to the main body and covers the inner cavity, one end of the main body far from the connecting portion is provided with an extension toward the rear cover, and the extension covers the end of the rear cover far from the connecting portion.

11. The electronic cigarette according to claim 10, wherein the rear cover and the extension far from one end of the connecting portion are integrally connected in a curved smooth transition manner.

12. The electronic cigarette according to claim 10, wherein the main body comprises a middle frame and a front case, one end of the middle frame is provided with a connecting portion fixedly connected to the external load, and the other end thereof encircles an inner cavity in which an internal electronic component is installed together with the front case, the rear cover is fixedly installed to the middle frame and covers the inner cavity, the extension is provided on the middle frame, the extension extends toward the rear cover and the front case, and covers the ends of the front case and the rear cover.

13. The electronic cigarette according to claim 12, wherein the inner cavity is further provided with at least one light source electrically connected to the electronic component, the front case is further provided with at least one light transmitting portion, and the ray of light emitted by each of the light sources is at least partially transmitted from the light transmitting portion; and/or the inner cavity is further provided with a plug terminal for the charging and data transmission of the battery assembly, the plug terminal is electrically connected to the electronic component, and the middle frame is provided with a plug port exposing the plug terminal.

14. The electronic cigarette according to claim 10, wherein at least one connecting buckle and at least one connecting female buckle are provided at both ends of one of the main body and the rear cover, respectively, at least one connecting neck and at least one connecting sub-buckle are correspondingly provided at both ends of the other of the main body and the rear cover, respectively, one of the connecting buckles is buckled to one of the connecting necks, one of the connecting female buckles is buckled to one of the connecting sub-buckles, and the rear cover is fixed to the main body.

15. The electronic cigarette according to claim 14, wherein at least one fixing female buckle is provided at both sides of one of the main body and the rear cover, and at least one fixing sub-buckle is provided at both sides of the other of the main body and the rear cover, one of the fixing female buckles is buckled to one of the fixing sub-buckles, and the rear cover is fixed to the main body.

16. The electronic cigarette according to claim 14, wherein a plurality of fixing female buckles are provided at both sides of one of the main body and the rear cover, respectively, a plurality of fixing sub-buckles are provided at both sides of the other of the main body and the rear cover, the plurality of fixing female buckles are oppositely provided at both sides of the main body or the rear cover and are provided at intervals away from the connecting portion, one of the fixing female buckles is buckled to one of the fixing sub-buckles, and the rear cover is fixed to the main body.

17. The electronic cigarette according to claim 14, wherein at least one limiting groove is provided at both sides of one of the main body and the rear cover, at least one limiting rib is provided at both sides of the other of the main body and the rear cover, one of the limiting ribs is inserted into one of the limiting grooves, and the rear cover is limited to the main body; and/or at least one positioning pin is provided in one of the main body and the rear cover, and at least one positioning slot is provided in the other of the main body and the rear cover, one of the positioning pins is inserted into one of the positioning slots, and the rear cover is positioned on the main body.

18. The electronic cigarette according to claim 14, wherein the rear cover has an arched cross section and defines an arched cavity, at least one limiting member is provided at both sides of the main body, respectively, and each of the limiting members abuts against the wall of the inner cavity of the arched cavity when the rear cover is buckled to the main body.

* * * * *